United States Patent
Liu et al.

(10) Patent No.: US 8,330,169 B2
(45) Date of Patent: Dec. 11, 2012

(54) MULTI-GAS SENSOR AND METHOD OF FABRICATING THE SENSOR

(75) Inventors: Wen-Chau Liu, Tainan (TW); Huey-Ing Chen, Tainan (TW); Tsung-Han Tsai, Tainan (TW); Tai-You Chen, Tainan (TW); Chung-Fu Chang, Tainan (TW); Chi-Hsiang Hsu, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 13/177,551

(22) Filed: Jul. 6, 2011

(65) Prior Publication Data
US 2012/0007099 A1 Jan. 12, 2012

(30) Foreign Application Priority Data
Jul. 6, 2010 (TW) .............................. 99122195 A

(51) Int. Cl.
*H01L 29/66* (2006.01)
(52) U.S. Cl. ............................. 257/76; 438/49
(58) Field of Classification Search .................... 438/49; 257/76, E21.09, E29.166
See application file for complete search history.

(56) References Cited

U.S. PATENT DOCUMENTS

| | | | | |
|---|---|---|---|---|
| 6,418,784 B1* | 7/2002 | Samman et al. | ............. | 73/31.06 |
| 6,927,067 B2* | 8/2005 | Sandhu | ......................... | 436/151 |
| 2012/0138921 A1* | 6/2012 | Endo et al. | ...................... | 257/43 |

* cited by examiner

*Primary Examiner* — Thao P. Le
(74) *Attorney, Agent, or Firm* — Ditthavong Mori & Steiner, P.C.

(57) ABSTRACT

The present invention is a multi-gas sensor and a method for fabricating the multi-gas sensor.
The multi-gas sensor comprises a substrate, an epitaxial layer, a metal oxide layer, a first metal layer, a second metal layer and multiple third metal layers.
The method for fabricating the multi-gas sensor comprises steps of forming an epitaxial layer on a substrate; etching the epitaxial layer to form a first epitaxial structure and a second epitaxial structure a fixed distance from the first epitaxial structure; forming a metal oxide layer on the first epitaxial structure; forming a first metal layer that has at least two metal layers on the second epitaxial structure; forming a second metal layer a fixed distance from the first metal layer on the second epitaxial structure; forming third metal layers respectively on the metal oxide layer, the first metal layer and the second metal layer.

18 Claims, 10 Drawing Sheets

|  | Palladium (Pd) | Platinum (Pt) | Zinc Oxide (ZnO) |
|---|---|---|---|
| Hydrogen | O | O | O |
| Ammonia | X | O | O |
| Nitrite Dioxide | X | X | O |

Reactive O
Non-reactive X

Fig. 9

MULTI-GAS SENSOR AND METHOD OF FABRICATING THE SENSOR

FIELD OF THE INVENTION

The present invention is a multi-gas sensor and a method of fabricating the multi-gas sensor. Specifically, the multi-gas sensor is made of metals and semiconductors and is able to identify multiple gases.

BACKGROUND OF THE INVENTION

Gas sensors are sensors that sense gas and can be classified into categories of: catalytic combustion sensors, controlled potential electrolysis sensors, hot wire semiconductor sensors, metal oxide semiconductor sensors, etc.

Catalytic combustion sensors have low detection sensitivity and long response time and can sense gases only in high temperature environments.

Controlled potential electrolysis sensors have short life spans compared to other types of sensors.

Hot wire semiconductor sensors are fabricated on a silicon substrate. No gas sensors formed on silicon substrates can be operated in a high temperature environment due to a comparably low energy gap of silicon.

Metal oxide semiconductor sensors can be operated in high temperature and corrosive environments, have comparably short response time and low fabrication cost and can be easily combined with digital circuits to form a gas sensor network. Metal oxide semiconductor sensors are the most needed gas sensors and are widely used in almost every environment from homes to factories for sensing toxic or explosive gases.

However, conventional metal oxide semiconductor sensors have poor gas selectivity, i.e. can only sense a single gas instead of multiple gases simultaneously. Thus improving metal oxide semiconductor sensors to sense multiple gases simultaneously and maintain a good sensitivity is a research objective for researchers.

SUMMARY OF THE INVENTION

The objective of the present invention is to provide a multi-gas sensor and a method for fabricating the multi-gas sensor.

A multi-gas sensor in accordance with the present invention comprises a substrate, an epitaxial layer, a metal oxide layer, a first metal layer, a second metal layer and multiple third metal layers.

A method of fabricating a multi-gas sensor in accordance with the present invention comprises steps of forming an epitaxial layer on a substrate; etching the epitaxial layer to form a first epitaxial structure and a second epitaxial structure a fixed distance from the first epitaxial structure; forming a metal oxide layer on the first epitaxial structure; forming a first metal layer with at least two metal layers on the second epitaxial structure; forming a second metal layer a fixed distance from the first metal layer on the second epitaxial structure; forming third metal layers on the metal oxide layer, the first metal layer and the second metal layer.

BRIEF DESCRIPTION OF THE DRAWINGS

FIG. 9 is a gas selectivity table of the third embodiment of the multi-gas sensor in accordance with the present invention.

DETAILED DESCRIPTION OF THE PRESENT INVENTION

Figure 1:
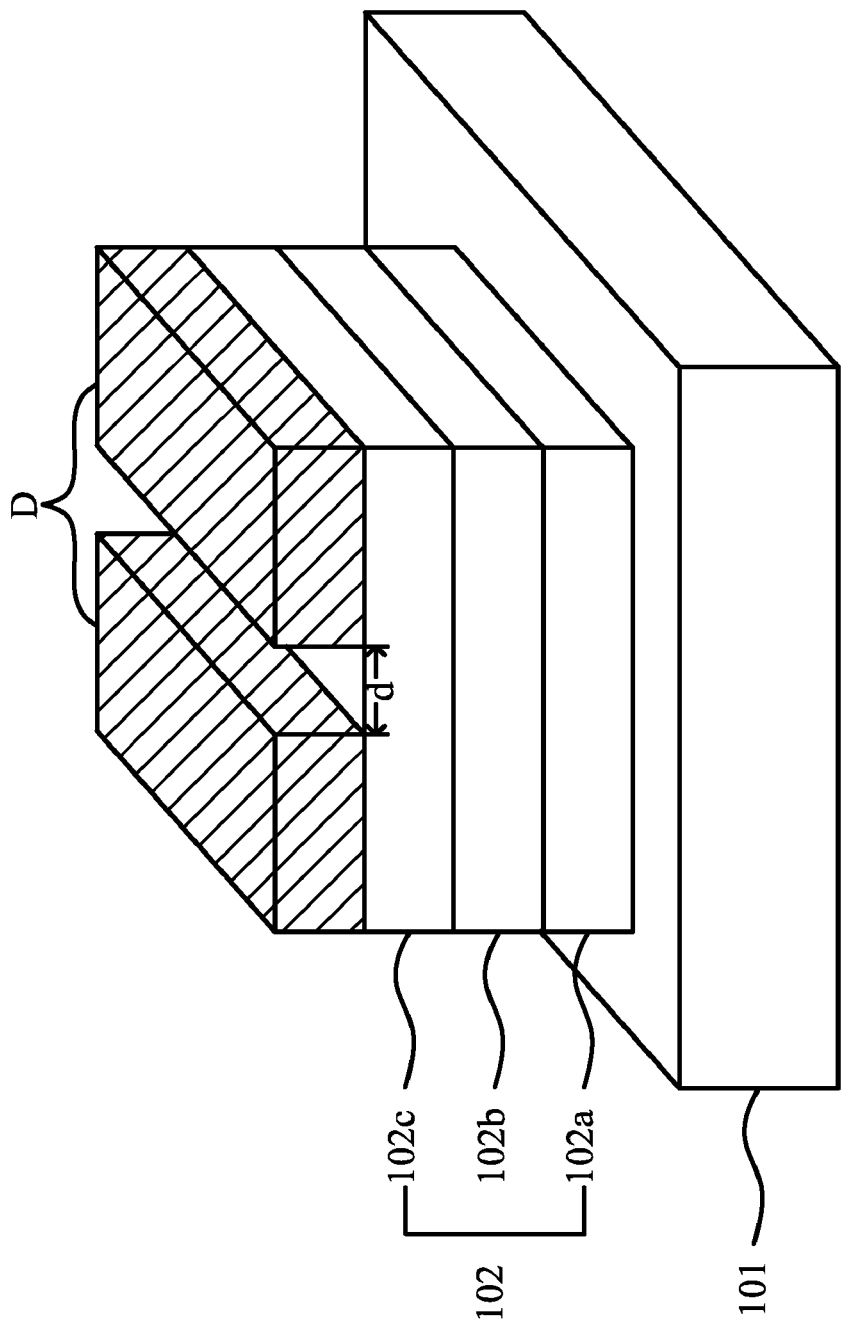
FIGS. 1 to 3 are schematic diagrams of a method of fabricating a first embodiment of a multi-gas sensor in accordance with the present invention.
Figure 2:
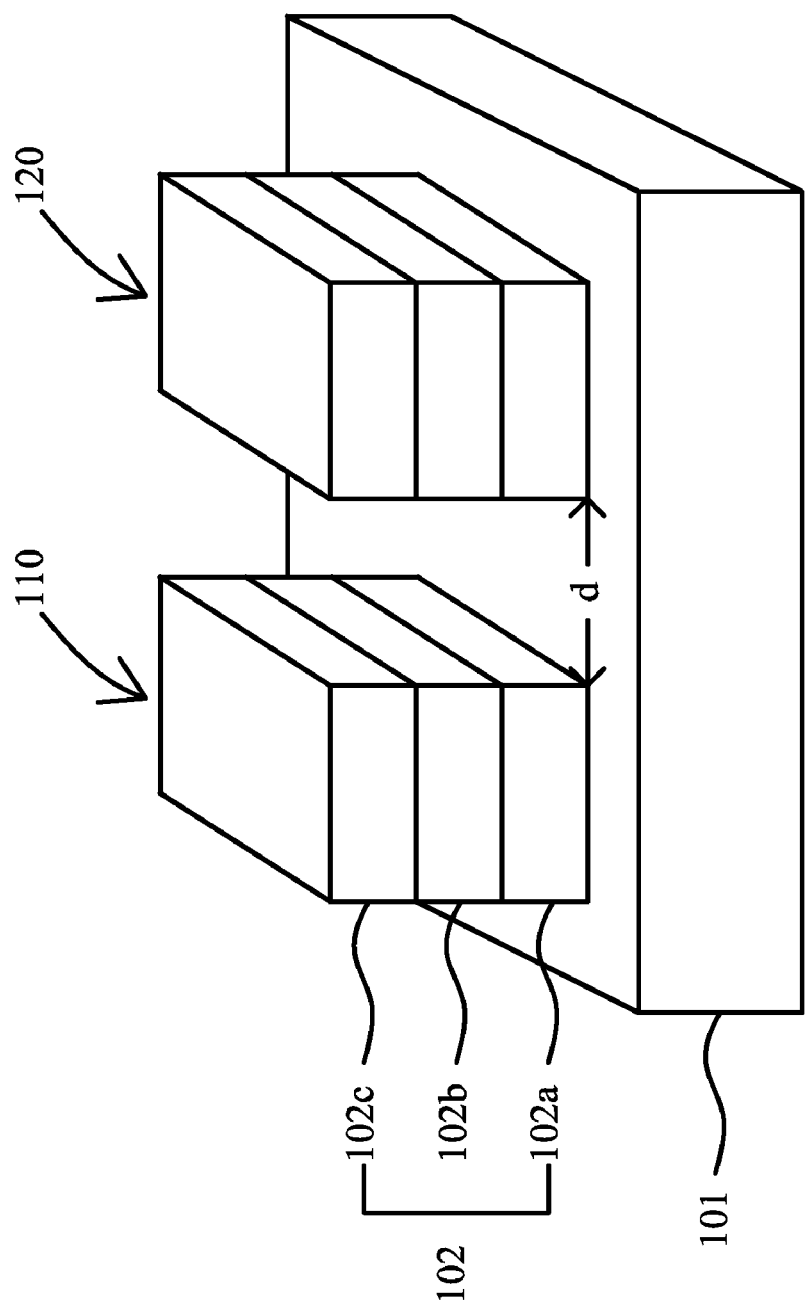
Figure 3:
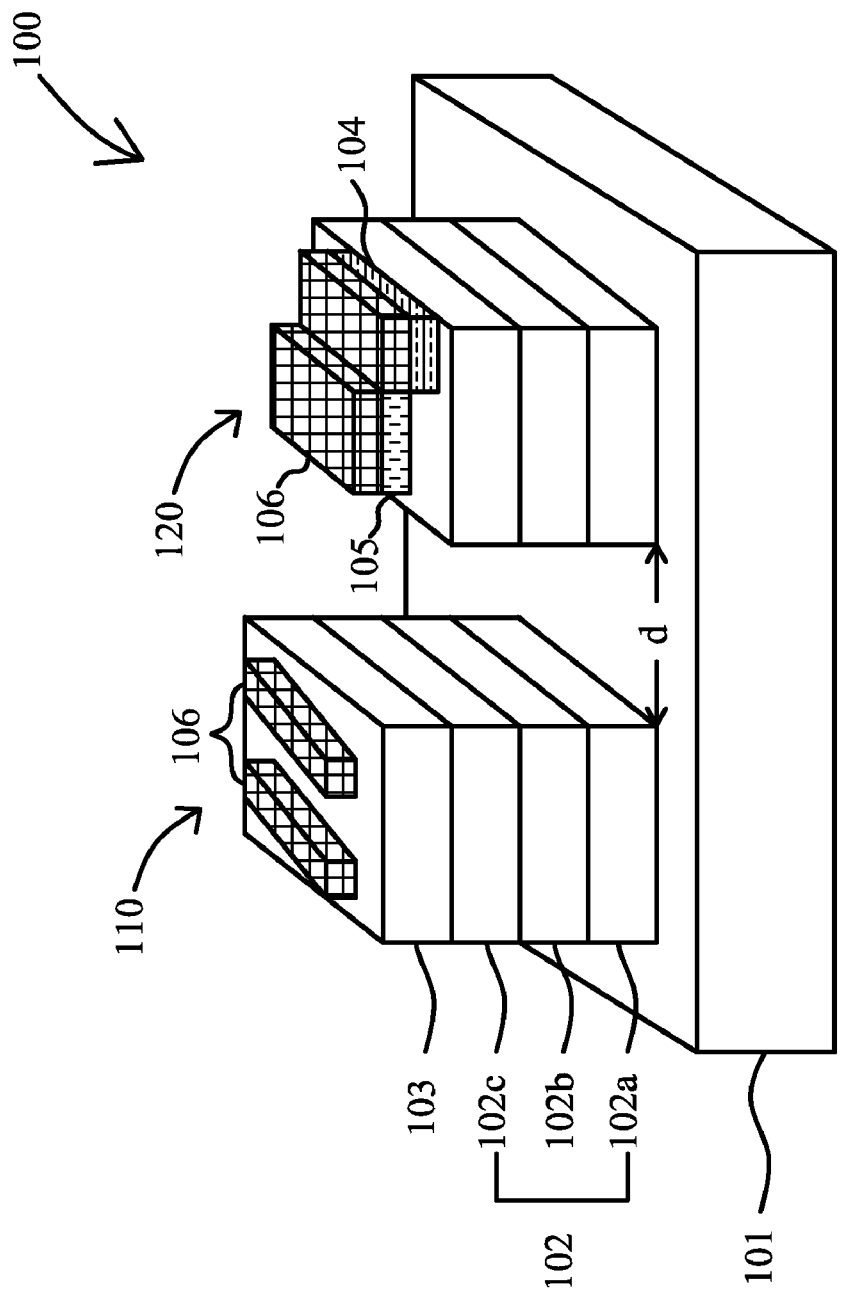

With reference to FIGS. 1 to 3, a first embodiment of a multi-gas sensor (100) in accordance with the present invention comprises a substrate (101), an epitaxial layer (102), a metal oxide layer (103), a first metal layer (104), a second metal layer (105) and third metal layers (106).

The substrate (101) is a sapphire substrate (101) and is 430 µm thick.

The epitaxial layer (102) comprises a first epitaxial structure (110) and a second epitaxial structure (120). The first epitaxial structure (110) is a fixed distance d from the second epitaxial structure (120). Each first and second epitaxial structure (110 and 120) comprises a nucleus layer (102a) that is an undoped Aluminum Nitrite (AlN) membrane and has a thickness can may range from 0.1 nm to 30 µm, a buffering layer (102b) that is an undoped Gallium Nitrite (GaN) membrane and has a thickness of 1.5 µm and an active layer (102c) that is an Aluminum Gallium Nitrite ($Al_xGa_{1-x}N$) membrane, has a thickness can may range from 1 nm to 15 µm, a value of x can may range from 0.01 to 0.5 and a carrier concentration n can may range from $1.6 \times 10^{16}$ $cm^{-3}$ to $1 \times 10^{20}$ $cm^{-3}$.

The metal oxide layer (103) can be a Zinc Oxide (ZnO), a Titanium Dioxide ($TiO_2$), a Tin Dioxide ($SnO_2$), a Tungsten Oxide ($WO_3$), a Nickel Oxide (NiO), an Iron Oxide ($Fe_2O_3$), a Magnesium Oxide (MgO), a Cobalt Oxide ($Co_3O_4$) or an Indium Oxide ($In_2O_3$) membrane, is formed on the active layer (102c) of the first epitaxial structure (110) and has a thickness that can may range from 1 nm to 50 µm. The metal oxide layer (103) can sense reducing and oxidizing gases and makes the multi-gas sensor able to determine different gases.

The first metal layer (104) is an Ohmic contact metal layer, is formed on the active layer (102c) of the second epitaxial structure (120) and comprises at least two metal layers that can may be Titanium/Aluminum (Ti/Al), Titanium/Aluminum/Platinum/Gold (Ti/Al/Pt/Au) or Chromium/Gold (Cr/Au). Titanium is 0.01 µm to 100 µm thick, Aluminum is 0.01 µm to 500 µm thick, Platinum is 0.01 µm to 100 µm thick, Gold is 0.01 µm to 500 µm thick, and Chromium is 0.01 µm to 200 µm thick.

The second metal layer (105) is a Schottky contact metal layer, can may be a Palladium (Pd), a Platinum (Pt), a Nickel (Ni), a Rhodium (Rh) or an Iridium (Ir) membrane, is formed on the active layer (102c) of the second epitaxial structure (120), is a fixed distance from the first metal layer (104) and has a thickness can may range from 0.1 nm to 200 µm. If the second metal layer (105) is a Palladium (Pd) membrane, the Palladium metal senses multiple gases and makes the multi-gas sensor (100) able to determine existence of Hydrogen ($H_2$). If the second metal layer (105) is a Platinum (Pt) membrane, the Platinum (Pt) metal senses Hydrogen ($H_2$) and Ammonia ($NH_3$) and makes the multi-gas sensor (100) able to determine existence of other gases.

The third metal layers (106) are Ohmic contact metal layers, can may be Platinum (Pt), Gold (Au), Palladium (Pd), Nickel (Ni) or Aluminum (Al) membranes, are formed on the metal oxide layer (103), the first metal layer (104) and the second metal layer (105), are the input and output ports of electrical signals of the multi-gas sensor (100), is a fixed distance from each adjacent third metal layer (106) and have thickness can may range from 0.01 μm to 100 μm.

Figure 4:
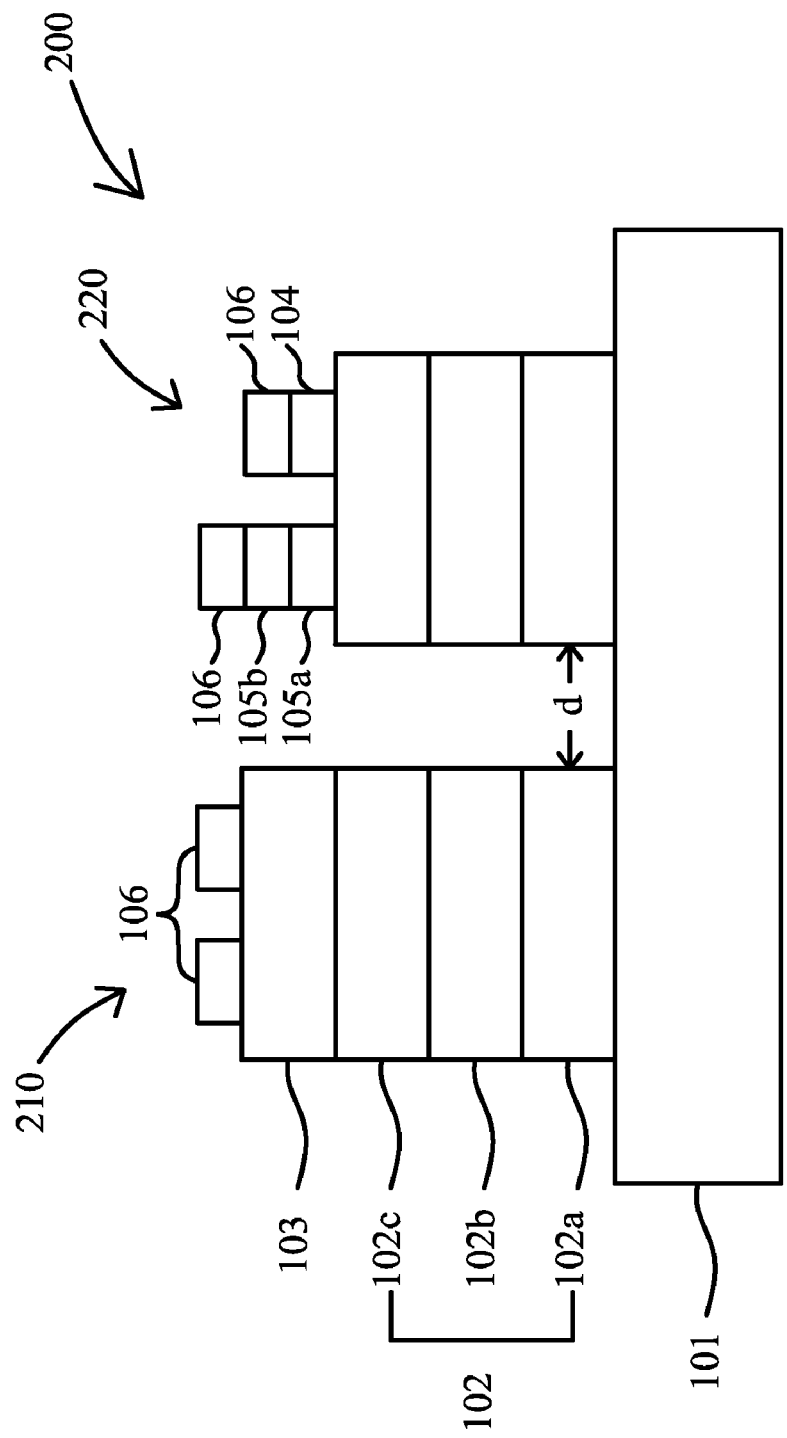
FIG. 4 is a side view of a second embodiment of a multi-gas sensor in accordance with the present invention.

With reference to FIG. 4, a second embodiment of the multi-gas sensor (200) in accordance with the present invention comprises a substrate (101), an epitaxial layer (102), a metal oxide layer (103), a first metal layer (104), two second metal layers (105a and 105b) and multiple third metal layers (106).

The substrate (101) is a sapphire substrate (101) and is 430 μm thick.

The epitaxial layer (102) comprises a first epitaxial structure (210) and a second epitaxial structure (220) that is a distance d from the first epitaxial structure (210). Each first and second epitaxial structure (110 and 120) comprises a nucleus layer (102a) that is an undoped Aluminum Nitrite (AlN) membrane and has a thickness can may range from 0.1 nm to 30 μm, a buffering layer (102b) that is an undoped Gallium Nitrite (GaN) membrane and has a thickness of 1.5 μm and an active layer (102c) that is an Aluminum Gallium Nitrite ($Al_xGa_{1-x}N$) membrane, has a thickness can may range from 1 nm to 15 μm, a value of x can may range from 0.01 to 0.5 and a carrier concentration n can may range from $1.6\times10^{16}$ $cm^{-3}$ to $1\times10^{20}$ $cm^{-3}$.

The metal oxide layer (103) can be a Zinc Oxide (ZnO), a Titanium Dioxide ($TiO_2$), a Tin Dioxide ($SnO_2$), a Tungsten Oxide ($WO_3$), a Nickel Oxide (NiO), an Iron Oxide ($Fe_2O_3$), a Magnesium Oxide (MgO), a Cobalt Oxide ($Co_3O_4$) or an Indium Oxide ($In_2O_3$) membrane, is formed on the active layer (102c) of the first epitaxial structure (210) and has a thickness that can may range from 1 nm to 50 μm. The metal oxide layer (103) can sense reducing and oxidizing gases and makes the multi-gas sensor able to determine different gases.

The first metal layer (104) is an Ohmic contact metal layer, is formed on the active layer (102c) of the second epitaxial structure (220) and comprises at least two metal layers that can may be Titanium/Aluminum (Ti/Al), Titanium/Aluminum/Platinum/Gold (Ti/Al/Pt/Au) or Chromium/Gold (Cr/Au). Titanium is 0.01 μm to 100 μm thick, Aluminum is 0.01 μm to 500 μm thick, Platinum is 0.01 μm to 100 μm thick, Gold is 0.01 μm to 500 μm thick, and Chromium is 0.01 μm to 200 μm thick.

The two second metal layers (105a and 105b) are Schottky contact metal layers, are respectively a Platinum (Pt) membrane and a Palladium (Pd) membrane, are formed sequentially bottom-up on the active layer (102c) of the second epitaxial structure (220) and are a fixed distance from the first metal layer (104). The multi-gas sensor (200) determines existence of Hydrogen ($H_2$) by allowing Hydrogen ($H_2$) to pass through the Palladium (Pd) metal layer (105b) and detecting the Hydrogen gas ($H_2$) in the Platinum (Pt) layer (105a).

The third metal layers (106) are Ohmic contact metal layers, can may be Platinum (Pt), Gold (Au), Palladium (Pd), Nickel (Ni) or Aluminum (Al) membranes, are formed on the metal oxide layer (103), the first metal layer (104) and the second metal layer (105a and 105b), are the input and output ports of electrical signals of the multi-gas sensor (200), are a fixed distance from each adjacent third metal layer (106) and have thickness can may range from 0.01 μm to 100 μm.

Figure 5:
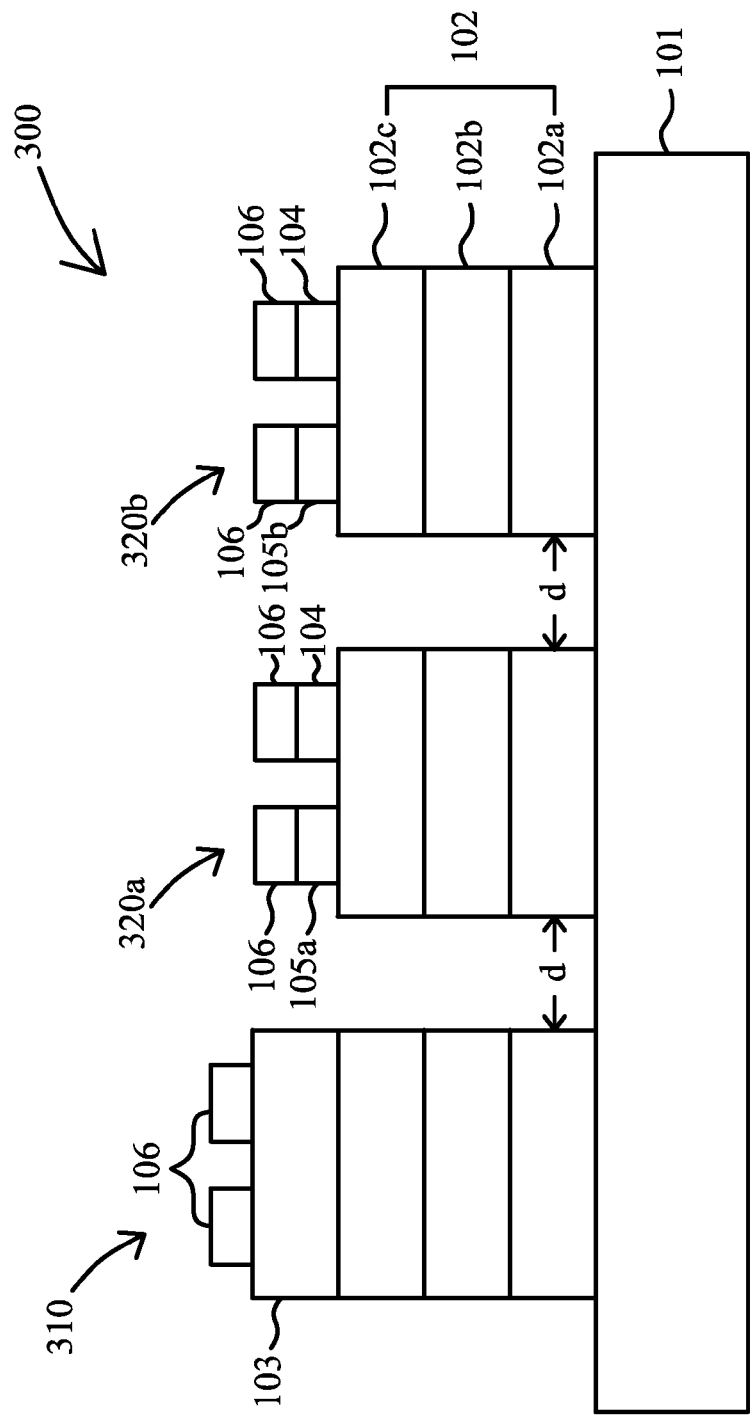
FIG. 5 is a side view of a third embodiment of a multi-gas sensor in accordance with the present invention.

With reference to FIG. 5, a third embodiment of the multi-gas sensor (300) in accordance with the present invention comprises a substrate (101), an epitaxial layer (102), a metal oxide layer (103), a first metal layer (104), multiple second metal layers (105a and 105b) and multiple third metal layers (106).

The substrate (101) is a sapphire substrate (101) and is 430 μm thick.

The epitaxial layer (102) comprises a first epitaxial structure (310) and two second epitaxial structures (320a and 320b). The first epitaxial structure (310) is a fixed distance d from the second epitaxial structure (320a); The second epitaxial structure (320a) is a fixed distance d from the second epitaxial structure (320b). Each first and second epitaxial structure (310, 320a and 320b) comprises a nucleus layer (102a) that is an undoped Aluminum Nitrite (AlN) membrane and has a thickness can may range from 0.1 nm to 30 μm, a buffering layer (102b) that is an undoped Gallium Nitrite (GaN) membrane and has a thickness of 1.5 μm and an active layer (102c) that is an Aluminum Gallium Nitrite ($Al_xGa_{1-x}N$) membrane, has a thickness can may range from 1 nm to 15 μm, a value of x can may range from 0.01 to 0.5 and a carrier concentration n can may range from $1.6\times10^{16}$ $cm^{-3}$ to $1\times10^{20}$ $cm^{-3}$.

The metal oxide layer (103) can be a Zinc Oxide (ZnO), a Titanium Dioxide ($TiO_2$), a Tin Dioxide ($SnO_2$), a Tungsten Oxide ($WO_3$), a Nickel Oxide (NiO), an Iron Oxide ($Fe_2O_3$), a Magnesium Oxide (MgO), a Cobalt Oxide ($Co_3O_4$) or an Indium Oxide ($In_2O_3$) membrane, is formed on the active layer (102c) of the first epitaxial structure (310) and has a thickness that can may range from 1 nm to 50 μm. The metal oxide layer (103) can sense reducing and oxidizing gases and makes the multi-gas sensor able to determine different gases.

The first metal layer (104) is an Ohmic contact metal layer, is formed on the active layers (102c) of the second epitaxial structures (320a and 320b) and comprises at least two metal layers that can may be Titanium/Aluminum (Ti/Al), Titanium/Aluminum/Platinum/Gold (Ti/Al/Pt/Au) or Chromium/Gold (Cr/Au). Titanium is 0.01 μm to 100 μm thick, Aluminum is 0.01 μm to 500 μm thick, Platinum is 0.01 μm to 100 μm thick, Gold is 0.01 μm to 500 μm thick, and Chromium is 0.01 μm to 200 μm thick.

The second metal layer (105a) is a Schottky contact metal layer, can may be a Palladium (Pd), a Platinum (Pt), a Nickel (Ni), a Rhodium (Rh) or an Iridium (Ir) membrane, is formed on the active layer (102c) of the second epitaxial structure (320a), is a fixed distance from the first metal layer (104) and has a thickness can may range from 0.1 nm to 200 μm.

The third metal layers (106) are Ohmic contact metal layers, can may be Platinum (Pt), Gold (Au), Palladium (Pd), Nickel (Ni) or Aluminum (Al) membranes, are formed on the metal oxide layer (103), the first metal layer (104) and the second metal layer (105a and 105b), are the input and output ports of electrical signals of the multi-gas sensor (100), is a fixed distance from each adjacent third metal layer (106) and have thickness can may range from 0.01 μm to 100 μm.

Figure 6:
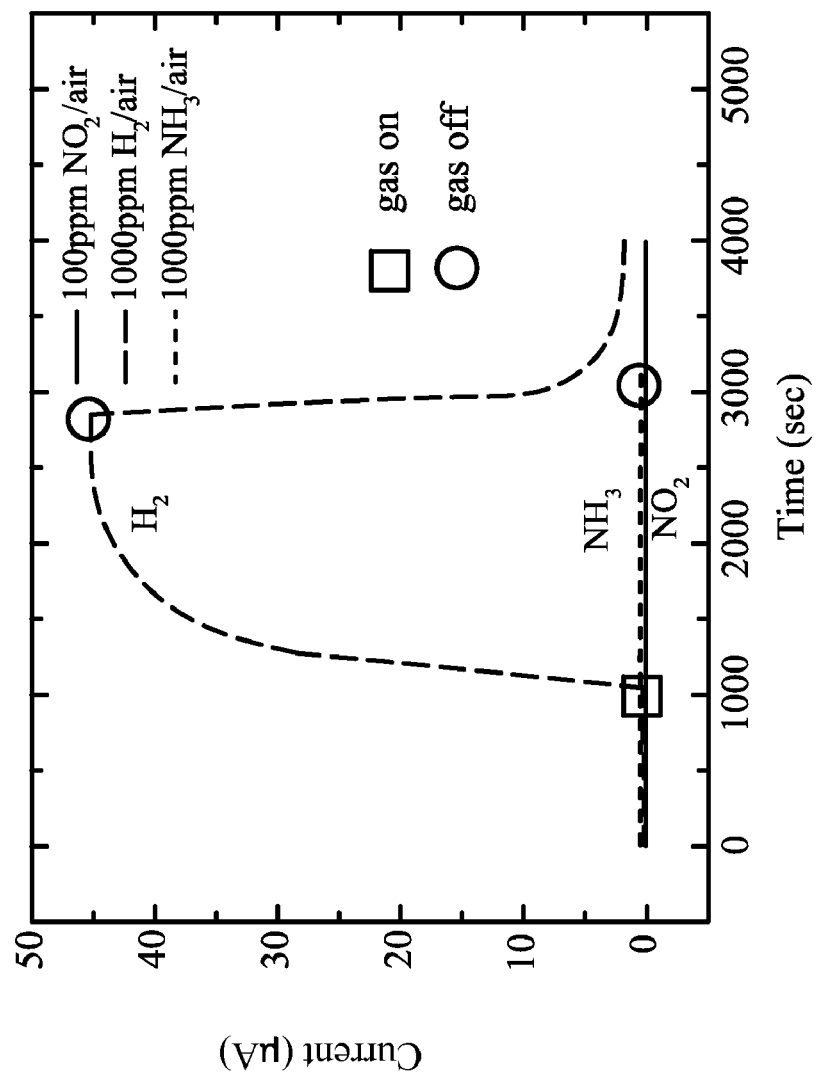
FIG. 6 is a transient response diagram of the third embodiment of the multi-gas sensor in accordance with the present invention under 25° C.

With reference to FIG. 6, the second epitaxial structure (320b) of the third embodiment of the multi-gas sensor (300) in accordance with the present invention has different transient responses for different gases under 25° C. The multi-gas sensor (300) operates in a biased voltage of 0.5V. As a 1000 ppm gas mixture of Hydrogen and air ($H_2$/air) passes through the multi-gas sensor (300), the second epitaxial structure (320b) has a dramatic current increment from $3.4\times10^{-7}$ A to $4.5\times10^{-5}$ A. However, as a 100 ppm gas mixture of Nitrogen Dioxide ($NO_2$) and air ($NO_2$/air) or a 1000 ppm mixture of Ammonia ($NH_3$) and air ($NH_3$/air) passes through the multi-gas sensor (300), the second epitaxial structure (320b) has a negligible current change.

The multi-gas sensor (300) senses Hydrogen gas ($H_2$) by a mechanism of chemically adsorbing Hydrogen ($H_2$) gas onto the second metal layer (105b) of the Platinum (Pt) membrane; dissociating the adsorbed Hydrogen gas ($H_2$) into Hydrogen atoms (H); diffusing the Hydrogen atoms (H) from the second metal layer (105b) to an interface of the second metal layer (105b) and the epitaxial layer (102). The diffused Hydrogen atoms (H) near the interface are polarized by a metal-semiconductor interface electric field and form a dipolar layer. The dipolar layer weakens the metal-semiconductor interface electric field, reduces a Schottky Barrier caused by the metal-semiconductor interface and results in a current increment.

Figure 7:
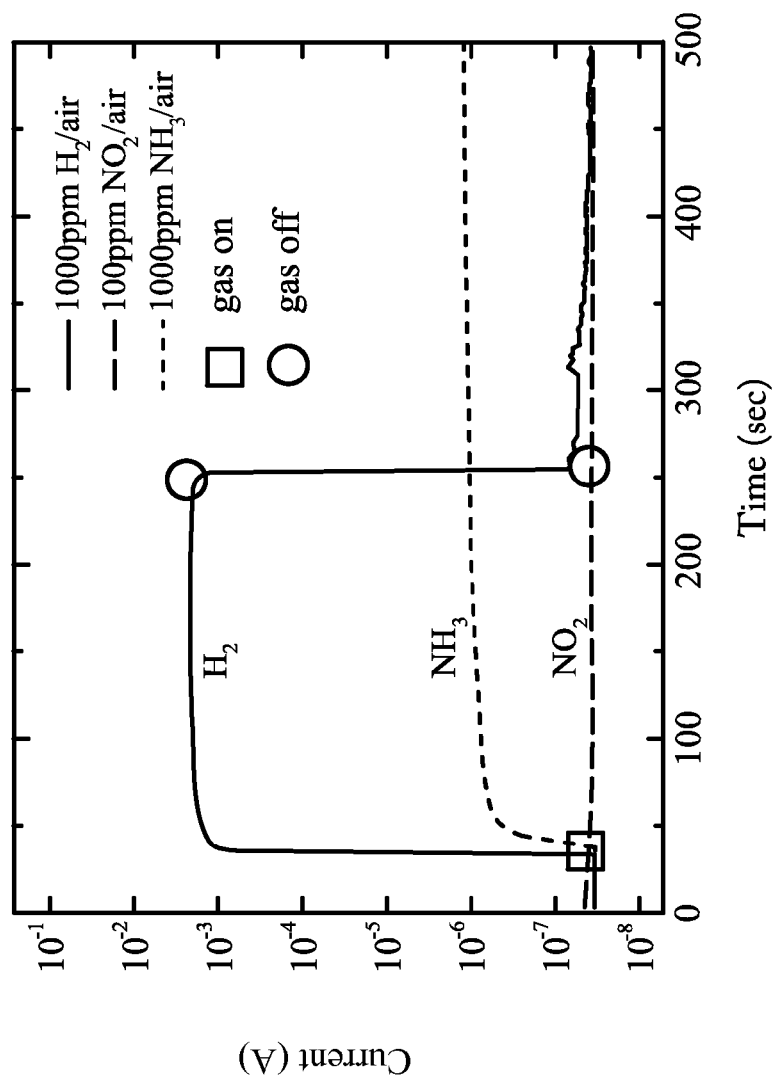
FIG. 7 is a transient response diagram of the third embodiment of the multi-gas sensor in accordance with the present invention under 150° C.

With reference to FIG. 7, the second epitaxial structure (320a) of the third embodiment of the multi-gas sensor (300) in accordance with the present invention has different transient responses for different gases under 150° C. The multi-gas sensor (300) operates in a biased voltage of 0.5V. As a 1000 ppm gas mixture of Hydrogen ($H_2$) and air ($H_2$/air) passes through the multi-gas sensor (300), the second epitaxial structure (320a) has a dramatic current increment from $3.3 \times 10^{-8}$ A to $1.83 \times 10^{-3}$ A. As a 1000 ppm gas mixture of Ammonia ($NH_3$) and air ($NH_3$/air) passes through the multi-gas sensor (300), the second epitaxial structure (320a) has a current increment from $3.3 \times 10^{-8}$ A to $1.1 \times 10^{-6}$ A. However, as a 100 ppm mixture of Nitrogen Dioxide ($NO_2$) and air ($NO_2$/air) passes through the multi-gas sensor (300), the second epitaxial structure (320b) has a negligible current change.

The multi-gas sensor (300) senses Ammonia gas ($NH_3$) by a mechanism of chemically adsorbing Ammonia gas ($NH_3$) onto the second metal layer (105a) of Palladium (Pd) membrane, dissociating the adsorbed Ammonia gas ($NH_3$) into Hydrogen atoms (H) and diffusing the Hydrogen atoms (H) from the second metal layer (105a) to an interface of the second metal layer (105b). The diffused Hydrogen atoms (H) near the interface are polarized by a metal-semiconductor interface electric field and form a dipolar layer. The dipolar layer weakens the metal-semiconductor interface electric field, reduces a Schottky Barrier caused by the metal-semiconductor interface and results in a current increment.

Figure 8:
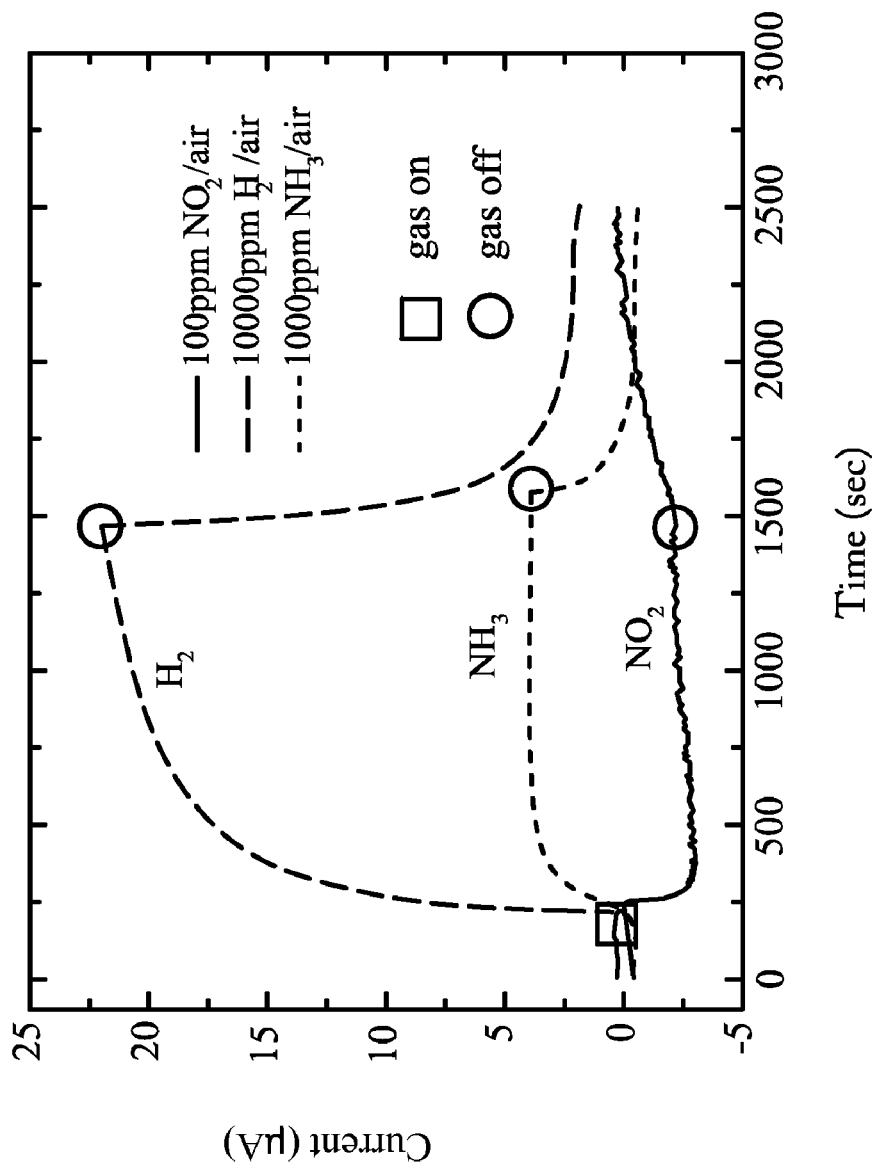
FIG. 8 is a transient response diagram of the third embodiment of the multi-gas sensor in accordance with the present invention under 300° C.

With reference to FIG. 8, the first epitaxial structure (310) of the third embodiment of the multi-gas sensor (300) in accordance with the present invention has different transient responses for different gases under 300° C. The multi-gas sensor (300) operates in a biased voltage of 0.5V. As a 100 ppm gas mixture of Nitrogen Dioxide ($NO_2$) and air ($NO_2$/air) passes through the first multi-gas sensor (300), the first epitaxial structure (310) has a current increment from $-1.29 \times 10^{-7}$ A to $-3.05 \times 10^{-6}$ A.

The multi-gas sensor (300) senses Nitrogen Dioxide gas ($NO_2$) by a mechanism of chemically adsorbing Nitrogen Dioxide gas ($NO_2$) onto the metal oxide layer (103) of Zinc Oxide (ZnO) membrane; dissociating the adsorbed Nitrogen Dioxide gas ($NO_2$) into oxygen ions (O). The dissociated oxygen ions combine electrons in a conduction band of the Zinc Oxide (ZnO) membrane and cause an electron density decrement, a resistance increment and a current decrement.

With reference to FIG. 9, the multi-gas sensor in accordance with the present invention identifies gases as a mixture of Hydrogen ($H_2$), Ammonia ($NH_3$) and Nitrogen Dioxide ($NO_2$).

Figure 10:
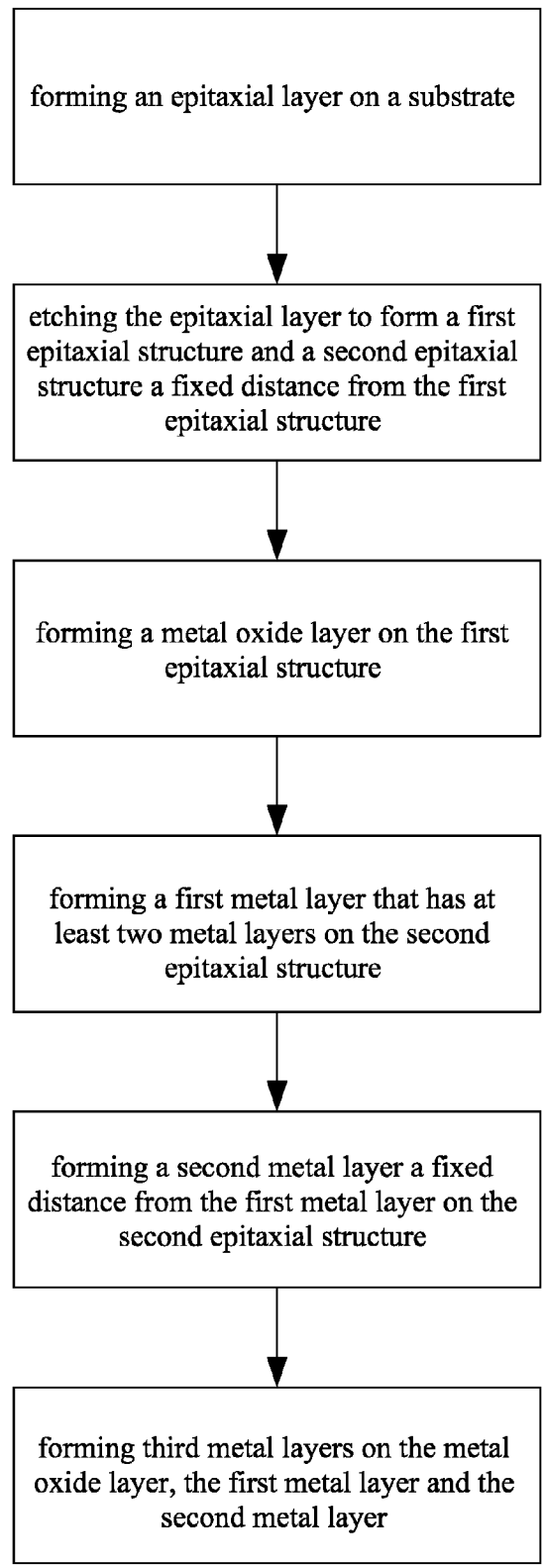
FIG. 10 is a flow chart of a method of fabricating a multi-gas sensor in accordance with the present invention.

With reference to FIG. 10, a method of fabricating a multi-gas sensor (100) comprises steps of forming an epitaxial layer (102) on a substrate (101), etching the epitaxial layer (102) to form a first epitaxial structure (110) and a second epitaxial structure (120) a fixed distance from the first epitaxial structure (110), forming a metal oxide layer (103) on the first epitaxial structure (102), forming a first metal layer (104) that has at least two metal layers on the second epitaxial structure (120), forming a second metal layer (105) a fixed distance from the first metal layer (104) on the second epitaxial structure (120), and forming third metal layers (106) on the metal oxide layer (103), the first metal layer (104) and the second metal layer (105).

The step of forming an epitaxial layer (102) on a substrate (101) comprises steps of forming a nucleus layer (102a) that is an undoped Aluminum Nitrite (AlN) membrane on a sapphire substrate (101) using metal organic chemical vapor deposition (MOCVD), forming a buffering layer (102b) that is an undoped Gallium Nitrite (GaN) membrane on the nucleus layer (102a) using MOCVD and forming an Aluminum Gallium Nitrite ($Al_xGa_{1-x}N$) active layer (102c) on the buffering layer (102b) using MOCVD.

The step of etching the epitaxial layer (102) to form a first epitaxial structure (110) and a second epitaxial structure (120) a fixed distance from the first epitaxial structure (110) comprises steps of plating Nickel (Ni) on the active layer (102c) to form multiple resistant layers (D) such that each resistant layer (D) is a distance d from each adjacent resistant layer (D); etching the epitaxial layer (102) to form a first epitaxial structure (110) and a second epitaxial structure (120) by using chlorine gas ($Cl_2$) with inductively coupled plasma reactive-ion etching (ICP-RIE) under a source power of 700 W and a radio-frequency power of 120 W; removing each resistant layer (D) using nitric acid ($HNO_3$) and removing oxides on the active layer (102c) using a mixture of 1:1 hydrofluoric (HF) and water ($H_2O$) liquid.

The step of forming a metal oxide layer (103) on the first epitaxial structure (102) forms a metal oxide layer (103) on the active layer (102c) using vacuum sputtering.

The step of forming a first metal layer (104) that has at least two metal layers on the second epitaxial structure (120) comprises steps of forming a first metal layer (104) on the second epitaxial structure (120) using thermal evaporation, annealing the first metal layer (104) in an inert gas environment by putting the multi-gas sensor (100) into a rapid thermal annealing (RTA) system under an annealing temperature of 900° C. and a response time of 300 seconds so that the first metal layer (104) can be diffused into the buffering layer (102b) to form a good Ohmic contact. The annealing temperature and the response time can range from 200° C. to 900° C. and 1 second to 50 minutes, respectively.

The step of forming a second metal layer (105) a fixed distance from the first metal layer (104) on the second epitaxial structure (120) forms a second metal layer (105) on the second epitaxial structure (120) and the active layer (102c) a fixed distance from the first metal layer (104).

The step of a forming third metal layers (106) on the metal oxide layer (103), the first metal layer (104) and the second metal layer (105) forms a third metal layer (106) on the metal oxide layer (103), the first metal layer (104) and the second metal layer (105) such that each third metal layer (106) is a distance from each adjacent third metal layer (106).

What is claimed is:

1. A multi-gas sensor comprising
   a substrate;
   an epitaxial layer being formed on the substrate and having
      a first epitaxial structure and a second epitaxial structure being a fixed distance from the first epitaxial structure;
      a metal oxide layer being formed on the first epitaxial structure;

a first metal layer being formed on the second epitaxial structure and comprising at least two metal layers;

a second metal layer being formed on the second epitaxial structure and a fixed distance from the first metal layer; and third metal layers being formed on the metal oxide layer, the first metal layer and the second metal layer.

2. The multi-gas sensor as claimed in claim 1, wherein the epitaxial layer comprises two second epitaxial structures a fixed distance from each other.

3. The multi-gas sensor as claimed in claim 1, wherein the substrate is a sapphire substrate.

4. The multi-gas sensor as claimed in claim 1, wherein the first and second epitaxial structure comprise a nucleus layer, a buffering layer and an active layer.

5. The multi-gas sensor as claimed in claim 4, wherein the nucleus layer is a undoped Aluminum Nitrite (AlN) membrane having a thickness ranging from 0.1 nm to 30 μm.

6. The multi-gas sensor as claimed in claim 4, wherein the buffering layer is an undoped Gallium Nitrite (GaN) membrane having a thickness ranging from 0.1 nm to 30 μm.

7. The multi-gas sensor as claimed in claim 4, wherein the active layer is an N-type doped Aluminum Gallium Nitrite ($Al_xGa_{1-x}N$) membrane having a thickness ranging from 1 nm to 15 μm, a value of x ranging from 0.01 to 0.5 and a carrier concentration ranging from $1.6 \times 10^{16}$ $cm^{-3}$ to $1 \times 10^{20}$ $cm^{-3}$.

8. The multi-gas sensor as claimed in claim 1, wherein the metal oxide layer has a thickness ranging from 1 nm to 50 μm.

9. The multi-gas sensor as claimed in claim 8, wherein the metal oxide layer can be a Zinc Oxide (ZnO), a Titanium Dioxide ($TiO_2$), a Tin Dioxide ($SnO_2$), a Tungsten Oxide ($WO_3$), a Nickel Oxide (NiO), an Iron Oxide ($Fe_2O_3$), a Magnesium Oxide (MgO), a Cobalt Oxide ($Co_3O_4$) or an Indium Oxide ($In_2O_3$) membrane.

10. The multi-gas sensor as claimed in claim 1, wherein the first metal layer and the third metal layers are Ohmic contact metal layers and the second metal layer is a Schottky contact metal layer.

11. The multi-gas sensor as claimed in claim 1, wherein the multi-gas sensor comprises two second metal layers that are stacked to form the second epitaxial structure.

12. The multi-gas sensor as claimed in claim 2, wherein the multi-gas sensor comprises two second metal layers that are stacked to form on the second epitaxial structure.

13. The multi-gas sensor as claimed in claim 10, wherein the first metal layer comprises at least two metal layers that can be Titanium/Aluminum (Ti/Al), Titanium/Aluminum/Platinum/Gold (Ti/Al/Pt/Au) or Chromium/Gold (Cr/Au) and has a thickness of Titanium being 0.01 μm to 100 μm, Aluminum being 0.01 μm to 500 μm thick, Platinum being 0.01 μm to 100 μm thick, Gold being 0.01 μm to 500 μm thick and Chromium being 0.01 μm to 200 μm thick.

14. The multi-gas sensor as claimed in claim 10, wherein the second metal layer can be a Platinum (Pt), a Palladium (Pd), a Nickel (Ni) or Iridium membrane having a thickness ranging from 0.1 nm to 200 μm and the third metal layers can be a Platinum (Pt), a Palladium (Pd), a Nickel (Ni), a Gold (Au) or an Aluminum (Al) membrane having a thickness ranging from 0.01 μm to 100 μm.

15. A method of fabricating a multi-gas sensor comprising steps of forming an epitaxial layer on a substrate;

etching the epitaxial layer to form a first epitaxial structure and a second epitaxial structure a fixed distance from the first epitaxial structure;

forming a metal oxide layer on the first epitaxial structure;

forming a first metal layer that has at least two metal layers on the second epitaxial structure;

forming a second metal layer a fixed distance from the first metal layer on the second epitaxial structure; and forming third metal layers on the metal oxide layer, the first metal layer and the second metal layer.

16. The method of fabricating a multi-gas sensor as claimed in claim 15, wherein the step of forming an epitaxial layer on a substrate comprises steps of forming a nucleus layer that is an undoped Aluminum Nitrite (AlN) membrane on a sapphire substrate using a metal organic chemical vapor deposition (MOCVD);

forming a buffering layer that is an undoped Gallium Nitrite (GaN) membrane on the nucleus layer using MOCVD; and forming an Aluminum Gallium Nitrite ($Al_xGa_{1-x}N$) active layer on the buffering layer using MOCVD.

17. The method of fabricating a multi-gas sensor as claimed in claim 16, wherein the step of etching the epitaxial layer to form a first epitaxial structure and a second epitaxial structure a fixed distance from the first epitaxial structure comprises steps of plating Nickel (Ni) on the active layer to form multiple resistant layers such that each resistant layer a distance d from each adjacent resistant layer;

etching the epitaxial layer to form a first epitaxial structure and a second epitaxial structure by using chlorine gas ($Cl_2$) with inductively coupled plasma reactive-ion etching (ICP-RIE) under a source power of 700 W and a radio-frequency power of 120 W;

removing each resistant layer using nitric acid ($HNO_3$); and removing oxides on the active layer using a mixture of 1:1 hydrofluoric (HF) and water ($H_2O$) liquid.

18. The method of fabricating a multi-gas sensor as claimed in claim 15, wherein the step of forming a first metal layer that has at least two metal layers on the second epitaxial structure comprises steps of forming a first metal layer that has at least two metal layers on the second epitaxial structure using thermal evaporation;

annealing the first metal layer in an inert gas environment by putting the multi-gas sensor in a rapid thermal annealing (RTA) system under an annealing temperature of 900° C. and a response time of 300 seconds so that the first metal layer is diffused into the buffering layer to form a good Ohmic contact.

* * * * *